United States Patent
Ellis

(10) Patent No.: US 8,798,367 B2
(45) Date of Patent: Aug. 5, 2014

(54) OPTICAL IMAGER AND METHOD FOR CORRELATING A MEDICATION PACKAGE WITH A PATIENT

(75) Inventor: Duane Ellis, Medford, NJ (US)

(73) Assignee: Metrologic Instruments, Inc., Blackwood, NJ (US)

(*) Notice: Subject to any disclaimer, the term of this patent is extended or adjusted under 35 U.S.C. 154(b) by 266 days.

(21) Appl. No.: 13/018,078

(22) Filed: Jan. 31, 2011

(65) Prior Publication Data

US 2012/0195479 A1 Aug. 2, 2012

(51) Int. Cl.
*G06K 9/00* (2006.01)

(52) U.S. Cl.
USPC ........... 382/181; 382/117; 700/213; 700/216; 700/231; 700/242; 700/240; 700/236; 700/304; 700/219; 700/220

(58) Field of Classification Search
CPC .......... H04N 1/00326; H04N 1/00331; H04N 1/00244; H04N 2201/3202; H04N 2201/3226; H04N 2201/3269; H04N 2201/3278; H04N 1/00453; H04N 1/32304; H04N 2201/3205; H04N 2201/3259; H04N 2201/3266
USPC .......... 382/181, 117; 700/213, 216, 231, 242, 700/240, 236, 304, 219, 220
See application file for complete search history.

(56) References Cited

U.S. PATENT DOCUMENTS

| | | | |
|---|---|---|---|
| 6,535,637 B1 * | 3/2003 | Wootton et al. | 382/190 |
| 7,059,526 B1 | 6/2006 | Sullivan et al. | |
| 7,061,831 B2 | 6/2006 | De La Huerga | |
| 7,216,802 B1 | 5/2007 | De La Huerga | |
| 7,712,288 B2 | 5/2010 | Ramasubramanian et al. | |
| 7,792,349 B2 * | 9/2010 | Van Den Brink | 382/141 |
| 7,813,938 B2 | 10/2010 | Kusterbeck | |
| 7,815,123 B2 | 10/2010 | Conner et al. | |
| 7,837,093 B1 | 11/2010 | Leu et al. | |
| 7,837,107 B1 | 11/2010 | Leu et al. | |
| 8,271,128 B1 * | 9/2012 | Schultz | 700/236 |
| 8,302,370 B1 * | 11/2012 | Decker et al. | 53/415 |
| 2004/0104271 A1 * | 6/2004 | Martucci et al. | 235/472.01 |
| 2007/0265729 A1 | 11/2007 | Braun et al. | |
| 2008/0027291 A1 | 1/2008 | Williams-Hartman | |
| 2009/0048868 A1 | 2/2009 | Portnoy et al. | |
| 2009/0290030 A1 | 11/2009 | Gocho | |
| 2010/0038273 A1 * | 2/2010 | Johnson | 206/459.5 |

(Continued)

*Primary Examiner* — Mike Rahmjoo
(74) *Attorney, Agent, or Firm* — Additon, Higgins, Pendleton & Ashe, P.A.

(57) ABSTRACT

A system is provided to correlate a medication package with a prescribed medication for a patient. The medication package accommodates an intended patient medication. The system includes an optical imager adapted to read an encoded symbol character comprising encoded patient information and further adapted to image an attribute of the medication package. The optical imager comprises a two-dimensional image sensor array and an imaging lens for focusing an image on the two-dimensional image sensor array. The two-dimensional image sensor array has a plurality of pixels formed in a plurality of rows and columns of pixels. The optical imager further includes a digital link to transmit a segment of data. The segment of data includes the patient information encoded in the encoded symbol character and the attribute of the medication package. The system further includes a host computer connected to the digital link to receive the segment of data from the optical imager, and a database coupled to the host computer via a digital connection. The database correlates the segment of data to (a) a patient record, and (b) a medication package attribute library.

20 Claims, 4 Drawing Sheets

(56) References Cited

U.S. PATENT DOCUMENTS

| | | |
|---|---|---|
| 2010/0127073 A1 | 5/2010 | van Esch |
| 2010/0219097 A1 | 9/2010 | Ramasubramanian et al. |
| 2010/0241446 A1 | 9/2010 | Eckert et al. |
| 2010/0241456 A1 | 9/2010 | Miller et al. |
| 2010/0283601 A1 | 11/2010 | Tai et al. |
| 2010/0298975 A1 | 11/2010 | Heath et al. |
| 2011/0015945 A1* | 1/2011 | Addy ................. 705/3 |
| 2011/0261194 A1* | 10/2011 | Udani ............. 348/135 |
| 2011/0317004 A1* | 12/2011 | Tao ................. 348/135 |
| 2012/0065999 A1* | 3/2012 | Takatoku et al. ........... 705/3 |
| 2012/0084091 A1* | 4/2012 | Hanina et al. ............. 705/2 |

\* cited by examiner

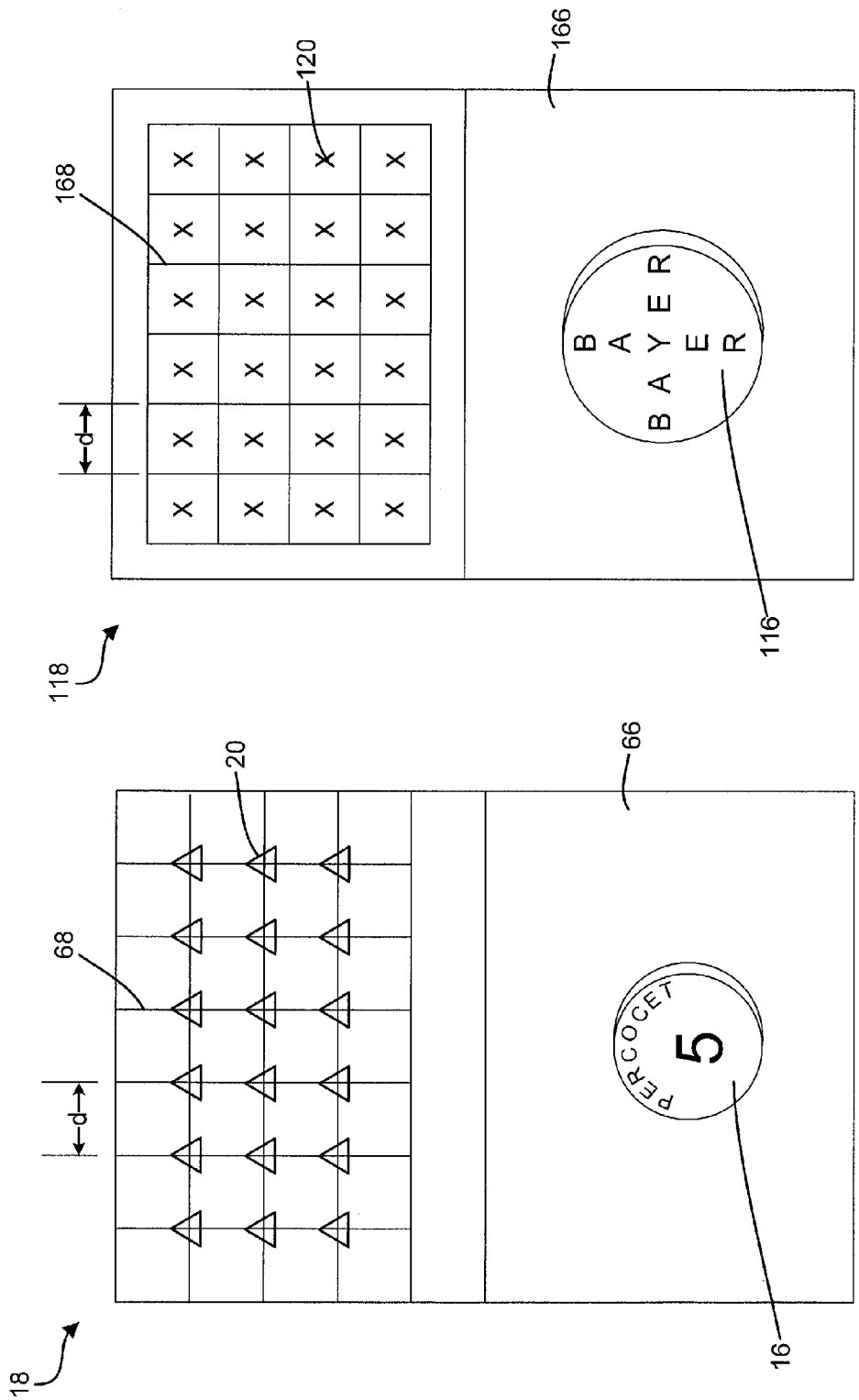

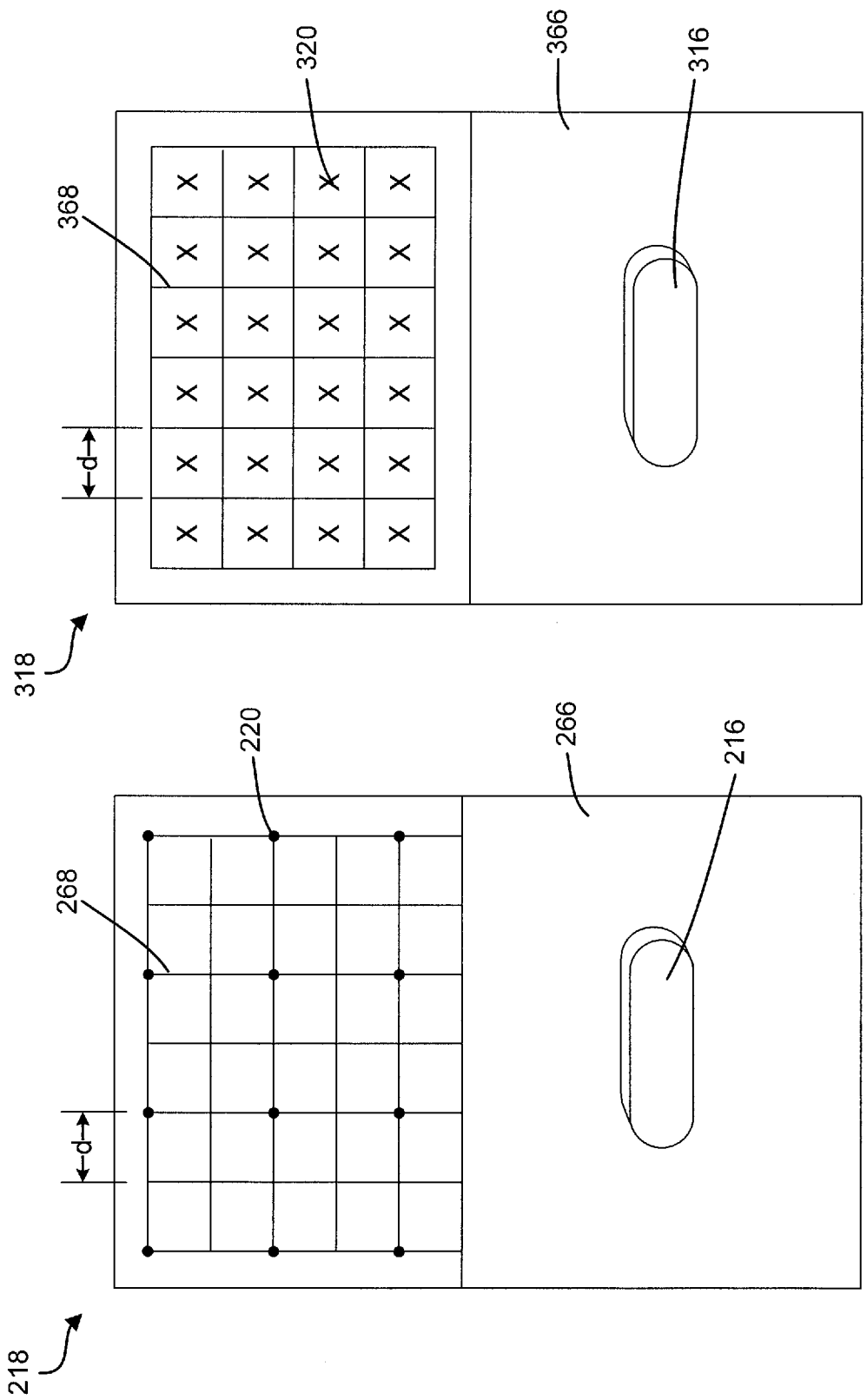

OPTICAL IMAGER AND METHOD FOR CORRELATING A MEDICATION PACKAGE WITH A PATIENT

FIELD OF THE INVENTION

This disclosure relates generally to optical imagers and, more specifically, to optical imagers adapted to identify medication packaging.

BACKGROUND OF THE INVENTION

In a hospital setting, a central pharmacy receives medications in bulk and dispenses them to individual patients. Unlike retail pharmacies, the medications in a hospital pharmacy generally are not dispensed in individual pill bottles with labels bearing patient names. Rather, the medications are carefully meted out by the pharmacy staff and sent to nursing stations where the nursing staff stores the medication until such time as the patient is ready to receive the medication.

Typically, the nursing staff verifies the patient identity and patient records prior to dispensing the medication to individual patients. In some hospitals, the patient wears a barcoded bracelet. The staff reads the bar code on the bracelet with a hand held bar code reader. From the information encoded in the bar code, patient information can be accessed, including medication dosages and schedules. The nursing staff then administers the medication to the patient. In other hospital settings, the bar coded information may be affixed to patient records (e.g., on a clipboard) near the hospital bed.

One drawback to this approach is that, although the pharmacy staff exercises extreme care in dispensing medication, and elaborate safeguards are in place to assure the correct medication is dispensed by the pharmacy staff, a "loss of custody" risk still exists as the medication transits from the hospital pharmacy to the individual patient. For example, in many instances, the pharmacy staff may dispense medication on trays or into paper cups destined for the patient. Such an uncontrolled chain of custody is fraught with risks of loss, mix-ups, inadvertent swapping, and intentional swapping (e.g., theft).

SUMMARY OF THE INVENTION

Therefore, in one aspect of the invention, a system is provided to correlate a medication package with a prescribed medication for a patient. The medication package accommodates an intended patient medication. The system includes an optical imager adapted to read an encoded symbol character comprising encoded patient information and further adapted to image an attribute of the medication package. The optical imager comprises a two-dimensional image sensor array and an imaging lens for focusing an image on the two-dimensional image sensor array. The two-dimensional image sensor array has a plurality of pixels formed in a plurality of rows and columns of pixels. The optical imager further includes a digital link to transmit a segment of data. The segment of data includes the patient information encoded in the encoded symbol character and the attribute of the medication package. The system further includes a host computer connected to the digital link to receive the segment of data from the optical imager, and a database coupled to the host computer via a digital connection. The database correlates the segment of data to (a) a patient record, and (b) a medication package attribute library.

In another aspect of the invention, a method for correlating a medication package with a patient is provided. The method includes the steps of providing an optical imager and a medication intended for a patient. The optical imager includes a two-dimensional image sensor array and an imaging lens for focusing an image on the two-dimensional image sensor array. The two-dimensional image sensor array has a plurality of pixels formed in a plurality of rows and columns of pixels. The medication is accommodated by a medication package having an attribute that is readable by the optical imager. Also provided is a database comprising an attribute library. The attribute library includes a plurality of candidate medications, each candidate medication having an associated package attribute. The method further includes the steps of capturing an image of the medication and package with the optical imager, processing the image to identify the attributes of the medication package, accessing the attribute library and correlating the imaged attributes of the medication package to the stored attributes of the candidate medications, and reporting, by the optical imager, a match between the imaged attribute of the medication package and one of the candidate medications.

In yet another aspect of the invention, a medication package is provided. The package includes a pouch adapted to hold a medication, and an attribute readable by an optical imager associated with the medication package. The attribute includes a grid printed on the pouch and symbols printed on the grid.

BRIEF DESCRIPTION OF THE DRAWINGS

The features described herein can be better understood with reference to the drawings described below. The drawings are not necessarily to scale, emphasis instead generally being placed upon illustrating the principles of the invention. In the drawings, like numerals are used to indicate like parts throughout the various views.

FIGS. 3A and 3B schematically illustrate one embodiment of patient medication packaging and corresponding attributes detectable by the imager of FIG. 1; and FIGS. 4A and 4B schematically illustrate another embodiment of patient medication packaging and corresponding attributes detectable by the imager of FIG. 1.

DETAILED DESCRIPTION OF THE INVENTION

Figure 1:
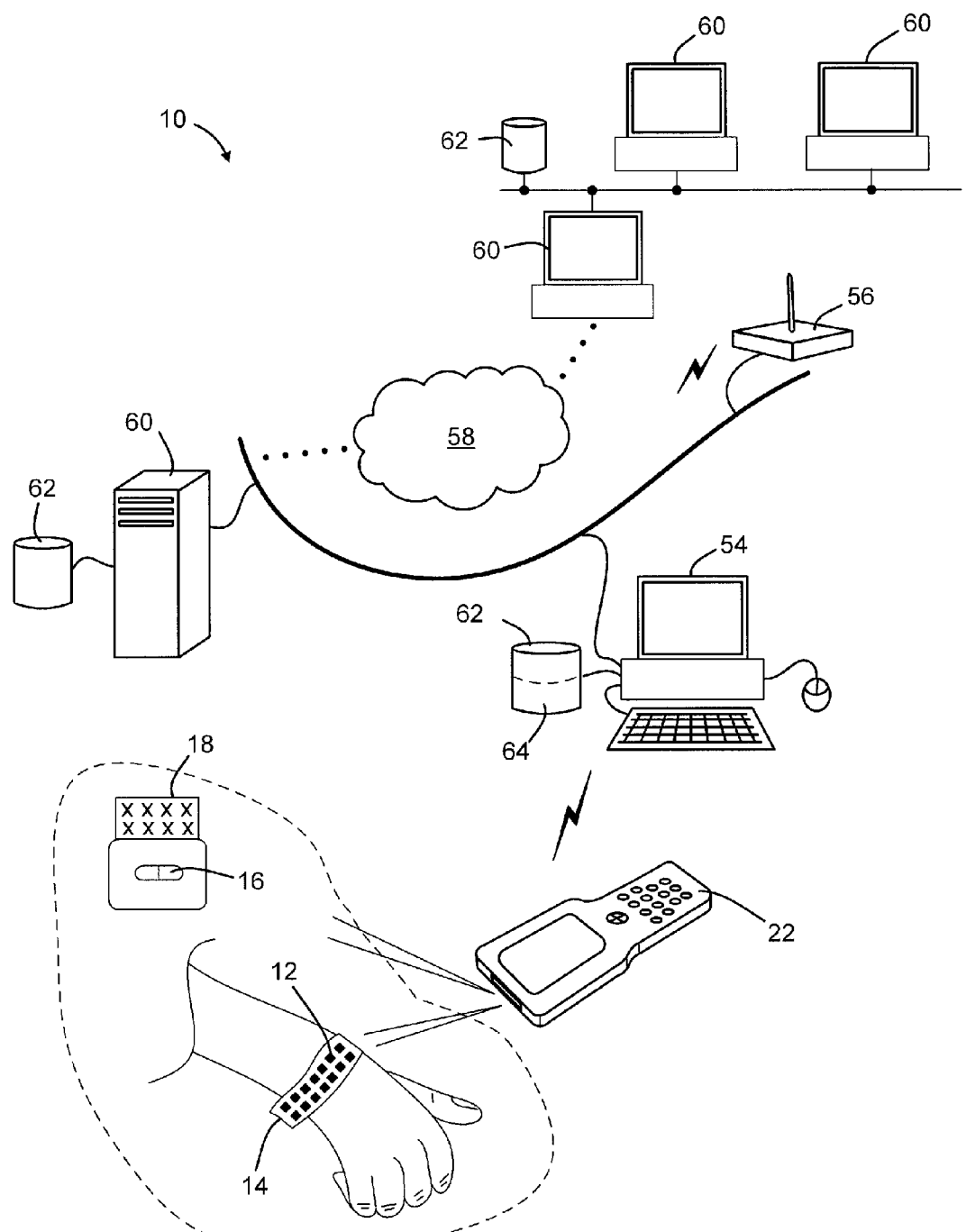
FIG. 1 is a schematic illustration of one embodiment of the inventive system.

A system 10 that in one aspect alleviates the risks associated with an uncontrolled chain of custody for patient medication is shown in FIG. 1. The system 10 is now described in the context of a hospital setting. A encoded symbol character 12 contains encoded information about a patient that may be correlated to a central database. The patient's encoded information, such as that encoded on a bar code, may be affixed to a patient clipboard in the vicinity of the patient or, more commonly, the encoded symbol character can be affixed to a patient wristband 14. The wristband 14 may comprise a plurality of bar code symbols situated across the wristband. Each encoded symbol character 12 can be an identical copy of each other.

As used herein, "encoded symbol character" is intended to denote a representation of a unit of information in a message, such as the representation in a bar code symbology of a single alphanumeric character. One or more encoded symbol characters can be used to convey information, such as the identification of the source and the model of a product, for example in a UPC bar code that comprises twelve encoded symbol characters representing numerical digits. Also, an encoded symbol character may be a non-alphanumeric character that has an agreed upon conventional meaning, such as the elements comprising bars and spaces that are used to denote the start, the end, and the center of a UPC bar code. The bars and spaces used to encode a character as an encoded symbol are referred to generally as "elements." For example an encoded character in a UPC symbol consists of four elements, two bars and two spaces. Similarly, encoded symbol characters can be defined for other bar code symbologies, such as other one-dimensional ("1-D") bar code systems including Code 39 and Code 128, or for stacked two-dimensional ("2-D") bar code systems including PDF417. Preferably, the encoded symbol characters 12 on the wristband can be a plurality of 2D bar codes.

The system 10 further includes a medication 16 intended for the patient. The medication may take many forms, but is preferably in pill form. In a hospital setting, a central pharmacy dispenses the patient medication for delivery to the patient. The medication 16 is packaged in a variety of ways to distinguish it from other medications. For example, if the medication 16 is in tablet form, the tablet can have a polymer- or polysaccharide-based coating with plasticizers and pigments included. The coating, particularly the pigments in the coating, can be manipulated to provide a distinctive appearance. The particular shape of the tablet, e.g., disk-shaped or caplet, is a further example of distinctive packaging. The tablet can also be stamped with symbols, letters, and numbers, which enable them to be identified.

The medication packaging may also include external packaging. Examples of external packaging include foil wraps or blister packs, paper wrapping, pouches, or even the small paper cups hospitals commonly use to deliver the medication to a hospital room.

Thus, each medication can have unique packaging attributes that separate it from other medications. In one embodiment of the current invention, a patient's medication 16 is placed in a package 18. In one example, the package 18 includes a paper pouch to hold the medication 16 in pill form. The paper is printed with a feature or attribute 20 that associates the package to the particular medication. Examples of various attributes will be described more fully below.

Medication having packaging with distinct attributes is not limited to pill form. In other examples, the medication can be in liquid form such as syrups, elixirs, suspensions, and emulsions. The liquid medication can have distinctive attributes such as color, or shape of container.

Figure 2:
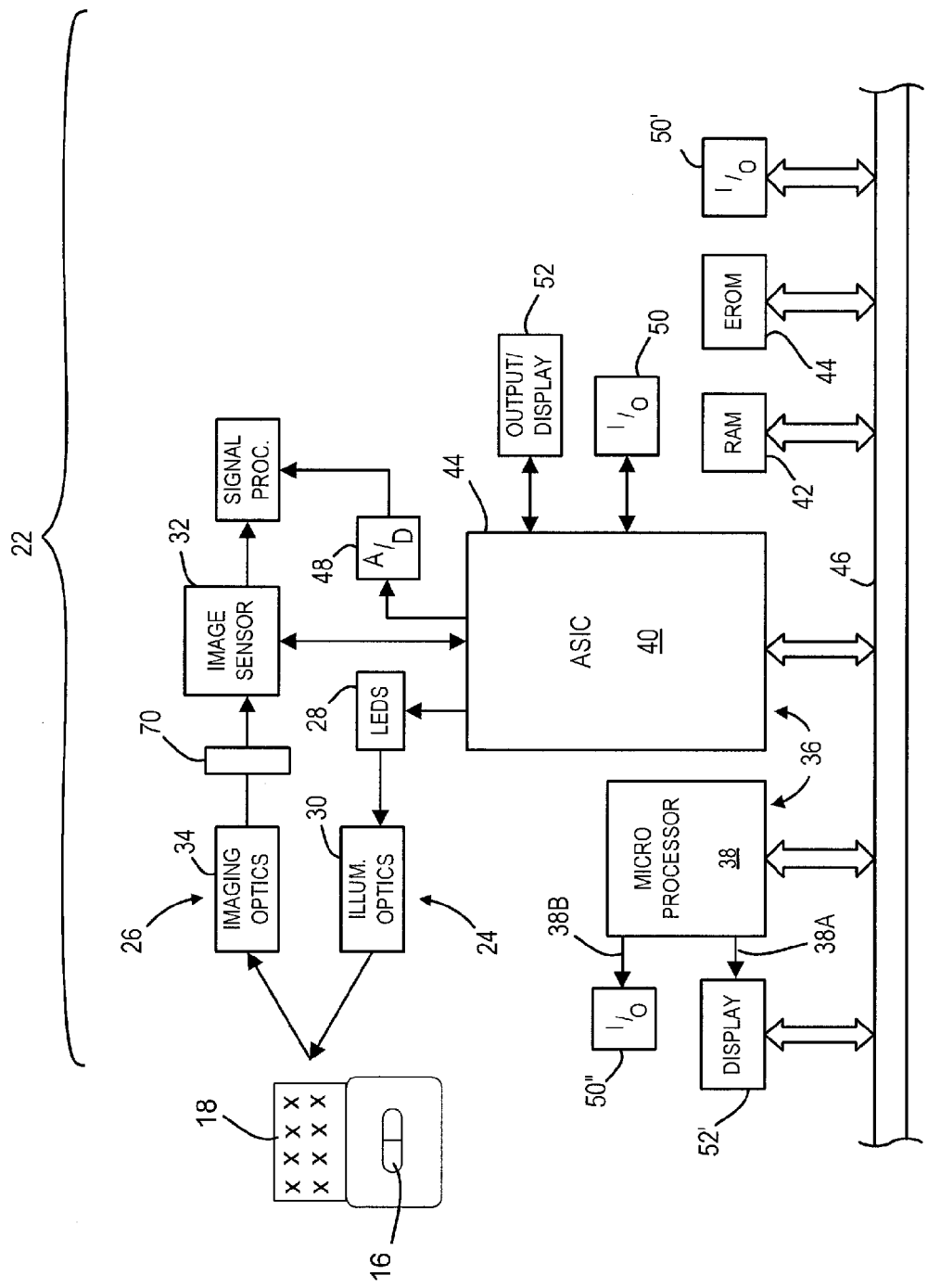
FIG. 2 is a block diagram of an exemplary hardware platform for implementation in an optical imager according to one embodiment of the present invention such as the optical imager of FIG. 1.

The system 10 further includes an optical imager 22 to read the encoded symbol character 12 associated with the patient, such as the bar coded wristband 14, and to image the attribute 20 associated with the medication package 18. Referring to FIG. 2, there is shown a block diagram of an optical imager 22 such as a CCD scanner. In general, an optical imager simultaneously illuminates all of the bars and spaces of a bar code symbol with light of a specific wavelength in order to capture an image for recognition and decoding purposes. Such scanners are commonly known as CCD scanners because they use CCD image detectors to detect images of the bar code symbols being read. As will be explained more fully below, FIG. 2 shows the basic structures that together comprise the general form of an imager that is suitable for use, and is generic to optical readers that use 1D image sensors and to optical readers that use 2D image sensors.

The optical imager 22 includes an illumination assembly 24 for illuminating the encoded symbol character 12, which may include a 1D or 2D bar code symbol, and the attribute 20 of the medication package 18. The optical imager 22 further includes an imaging assembly 26 for receiving an image of the encoded symbol character 12 and the attribute 20, and generating an electrical output signal indicative of the data optically encoded therein. Illumination assembly 24 may, for example, include an illumination source assembly 28, such as one or more LEDs, together with an illuminating optics assembly 30, such as one or more reflectors, for directing light from light source 28 in the direction of the character 12 and the attribute 20. Illumination assembly 24 may be eliminated, if ambient light levels are certain to be high enough to allow high quality images to be taken. Imaging assembly 26 may include an image sensor 32 having a plurality of pixels formed in a plurality of rows and columns of pixels, such as a 1D or 2D CCD, CMOS, NMOS, PMOS, CID or CMD solid state image sensor, together with an imaging optics assembly 34 for receiving and focusing an image of the character 12 or the attribute 20 onto image sensor 32.

The optical imager 22 of FIG. 2 also includes programmable control means 36 which preferably comprises an integrated circuit microprocessor 38 and an application specific integrated circuit or ASIC 40. Microprocessor 38 and ASIC 40 are both programmable control devices which are able to receive, output and process data in accordance with a stored program stored in either or both of a read/write random access memory or RAM 42 and an erasable read only memory or EROM 44. Processor 38 and ASIC 40 are also both connected to a common bus 46 through which program data and working data, including address data, may be received and transmitted in either direction to any circuitry that is also connected thereto. Processor 38 and ASIC 40 differ from one another, however, in how they are made and how they are used.

More particularly, processor 38 is preferably a general purpose, off-the-shelf VLSI integrated circuit microprocessor which has overall control of the circuitry of FIG. 2, but which devotes most of its time to decoding image data stored in RAM 42 in accordance with program data stored in EROM 44. Processor 40, on the other hand, is preferably a special purpose VLSI integrated circuit, such as a programmable logic or gate array, which is programmed to devote its time to functions other than decoding image data, and thereby relieve processor 38 from the burden of performing these functions.

The actual division of labor between processors 38 and 40 will naturally depend on the type of off-the-shelf microprocessors that are available, the type of image sensor which is used, the rate at which image data is output by imaging assembly 26, etc. There is nothing in principle, however, that requires that any particular division of labor be made between processors 38 and 40, or even that such a division be made at all. This is because special purpose processor 40 may be eliminated entirely if general purpose processor 38 is fast enough and powerful enough to perform all of the functions contemplated. It will, therefore, be understood that neither the number of processors used, nor the division of labor there between, is of any fundamental significance.

With processor architectures of the type shown in FIG. 2, a typical division of labor between processors 38 and 40 will be as follows. Processor 38 is preferably devoted primarily to the tasks of decoding image data, once such data has been stored in RAM 42, handling the menuing options and reprogramming functions, and providing overall system level coordination. Processor 40 is preferably devoted primarily to controlling the image acquisition process, the A/D conversion process and the storage of image data, including the ability to access memories 42 and 44 via a DMA channel. Processor 40 may also perform many timing and communication operations. Processor 40 may, for example, control the illumination of LEDs 28, the timing of image sensor 32 and an analog-to-digital (A/D) converter 48, the transmission and reception of data to and from a processor external to the optical imager 22, through an RS-232 (or other) compatible I/O device 50 and the outputting of user perceptible data via an output device 52, such as a beeper, a good read LED and/or a display which may be, for example, a liquid crystal display. Other examples of output devices 52 include tactile feedback technologies such as haptic interfaces that apply forces, vibrations, and motions, for example, to the operator of the optical imager 22. Control of output, display and I/O functions may also be shared between processors 38 and 40, as suggested by bus driver I/O and output/display devices 50' and output device 52' or may be duplicated, as suggested by microprocessor serial I/O ports 38A and 38B and I/O and display devices 50" and 52'. As explained earlier, the specifics of this division of labor is of no significance.

Referring back to FIG. 1, one or more bar code imagers 22 communicate with a host computer 54 by any method suitable for digital communications between a bar code imager and a computer. Where host computer 54 is co-located with the optical imager 22, communications options include hard wiring by serial, parallel, USB, Firewire, Ethernet, or other wired interface, copper wire, coaxial cable, optical fiber, twisted wire, shielded cable, or shielded twisted wire and a wireless interface 56. Both wired and wireless interface 56 can further be connected to the Internet 58.

Suitable wireless standards as known in the art of digital wireless communication range from data over cell phone to personal area networks, including GSM (Global System for Mobile), GPRS (General Packet Radio Service), EDGE (Enhanced Data Rates for GSM Evolution), W-CDMA (FDD) (Wideband Code Division Multiple Access Frequency Division Duplex), TD-SCDMA (Time Division-Synchronous Code Division Multiple Access), HSDPA (High Speed Downlink), TIA/EIA-95A/B (cdmaOne System), cdma2000 (1xRTT) (1× Radio Telephone Technology), 1xEV-DO, (1× Evolution Data Only; High Rate Packet Data), 1xEV-DV, (1× Evolution Data and Voice), iDEN (Integrated Dispatch Enhanced Network), TETRA (Terrestrial Trunked Radio), Bluetooth (Wireless Personal Area Network; PAN), IEEE 802.11a/g/h/j (Wireless Local Area Network; LAN), IEEE 802.15.3a (UWB), (Ultra Wideband Personal Area Network; PAN), IEEE 802.16a/e (Wireless Metropolitan Area Network (MAN). In addition to conventional amplitude (AM), frequency modulation (FM), frequency shift keying (FSK), and phase shift keying (PSK), other suitable data modulation types include GMSK, rotating 8PSK and higher, including 3π/8 rotating 8PSK, QPSK, 16QAM through 128QAM and higher, M16-QAM and higher, π/4 DQPSK, GFSK, DBPSK, CCK with DQPSK, subcarrier OFDM, including 52 subcarrier OFDM, Shaped Pulse or Frequency switched OFDM, and OFDM with QPSK. Other wireless radio frequency (RF) interfaces or wireless light interfaces, including visible and infrared light (IR) LED or laser light sources and detectors, and other light operated interfaces including line of sight or fiber optic connections can be used as well.

In the case of a co-located computer 54, the computer can be a desktop PC, laptop PC, Notebook PC, Tablet PC, hand held PC, PDA, or other wired or wireless computer. Similarly, optical imager 22 can further include computer 54. In this embodiment, computer 54 can communicate with other computers 60 via a wired or wireless connection. Such communication between a optical imager 22 and computers 60 can take place by a direct wired or wireless communication between the computers or by connection to a computer network accessible to both computers 54 and 60.

Also included in the system 10 is a database 62. The database 62 contains the data to correlate a patient's encoded symbol character 12 to the patient's information. The patient's information can include the patient's name, social security number, date of birth, a digital image of the patient, blood type, hospital identification number ("ID"), biometric identification information, and any other patient records associated with that patient, including the patient's address, phone number, emergency contact information, prescription history, treating physicians, guardian or health proxy contacts, medical treatment history, medical insurance information, current prescription medications, medication history, and names of identifying physicians, etc. One example of current prescription medications can include a prescription for the pain reliever Percocet, to be administered one tablet every 6 hours as needed for pain, with the total daily dose of acetaminophen not exceeding 4 grams.

Database 62 is typically a relational database as known in the art, but could be any suitable database for correlating information as listed above to the patient's encoded symbol character 12. It should be noted that a database 62 can also reside in any suitable type of memory within a portable data terminal (PDT), including RAM, ROM, EPROM, EEPROM, hard drive, optical drive, or any suitable disk drive. Database 62 can also reside in and be attached to a bar code reader such as can be incorporated into a PDT, in the form of a drive or memory "stick", a portable plug in memory unit comprising solid state or rotating disk memory.

The database 62 can also contain a medication package attribute library 64 to store a list of medications in supply at the hospital and their particular attributes for each of the medication packages. The attributes according to the present invention may correspond to attributes of a package containing an intended medication for a patient. The attributes can be imaged by the optical imager and decoded for comparison and correlation to the attributes stored in the attribute library. In one embodiment, the attribute library 64 contains a list of pain relievers, and the packaging attributes can include the pill shape and the printing stamped into the pill. For example, the narcotic pain reliever Percocet can have the following attributes 20 stored in the attribute library 64: white in color, round in shape, "PERCOCET" stamped into the outer diameter of one face, and the number "5" stamped in the center (to denote 5 mg oxycodone HCl/325 mg acetaminophen). In another example, the over-the-counter pain reliever Bayer aspirin can have the following attributes 20 stored in library 64: white in color, round in shape, and "BAYER" stamped vertically and horizontally across the tablet. In another example, the narcotic pain reliever Vicodin (e.g., 500 mg paracetamol and 5 mg hydrocodone) can have the following attributes 20 stored in library 64: white in color, caplet-shaped, and "VICODIN" stamped on one face. And in yet another example, the over-the-counter pain reliever tylenol aspirin can have the following attributes 20 stored in library 64: white in color, caplet-shaped, and "TYLENOL" stamped on one face.

In operation, a nurse or aide can use the optical imager 22 to scan the encoded symbol character 12 and the medication package 18. Once scanned, the coded information contained within the character 12 and the image of the attribute 20 can be relayed to computer 54 as a segment of data. In the case where computer 54 is included in the optical imager 22, the digital information is conveyed internally within the body of the imager 22. Otherwise, the optical imager 22 transmits the segment of data to computer 54 by any suitable method, including the exemplary communication methods previously discussed.

Computer 54 can comprise database 62 and further correlate and return one or more pieces of information based on the decoded bar code data and the image of the attribute, or more likely computer 54 further communicates with other computers 60, such as by a suitable computer network. Similarly, one or more computers 60 may further comprise database 62, or database 62 can reside on a remote computer, such as a remote computer server on a local or distant computer network including the Internet 58. There may also be multiple databases 62 where some patient information such as ID and medications may be on one database 62 as on or associated with a computer 60 in the local hospital, whereas other patient data, such as patient treatment history, can be accessed on another database 62. Or, the attribute library 64 can be stored in a separate database. In such cases, the one or more remote databases can be anywhere accessible by a computer network, such as anywhere on the Internet 58. The security of such a network can be enhanced by use of a virtual private network ("VPN") residing on the Internet. Various levels of VPN security can be implemented using a selection of private and public keys.

Following the connection to one or more databases 62, the patient information can be returned to computer 54 and displayed on a display associated with either computer 54 or on optical imager 22 for the nurse to see. The nurse can view just the patient ID information or in some embodiments can further access other information associated with that patient as needed from one or more databases 62 using a user interface on either on optical imager 22 or on computer 54. Such an interface can be graphical user interface ("GUI").

In addition to the medication package attributes being found on the medication itself, external packaging attributes of the medication can be stored in the attribute library 64. One example of external packaging attributes is shown in FIG. 3A in combination with FIG. 1. A medication package 18 issued by the hospital pharmacy includes a paper pouch 66 holding the medication 16 to be administered to the patient, which in the illustrated example is a Percocet pill. A grid 68 printed on the upper portion of the package 18 comprises squares spaced by a distance "d" of 0.25 inch in one example. Printed on the grid 68 is an attribute 20 that is readable by the optical imager 22. In the illustrated example, the attribute 20 is printed triangular symbols spaced 0.25 inch apart. The grid 68 pattern in the illustrated examples can also occupy the entire background of the pouch 66, such that the medication 16 is overlaid against the grid pattern background.

In one aspect, the pouches can be stored in the pharmacy in roll form, with each roll having specific attributes. The pharmacologist can simply tear off a pouch from an appropriate roll, deposit the medication therein, and send to the patient's room. In one example, a pouch 66 can have a red attribute 20 associated with narcotics, a blue attribute 20 associated with blood thinners, and a green attribute associated with heart medication.

Turning to FIG. 3B, a different medication package 118 issued by the hospital pharmacy holds an over-the-counter tablet 116 of Bayer aspirin. The pouch 166 has a grid 168 on the upper portion that comprises 0.25 inch squares but, unlike the example shown in FIG. 3B, the attribute 120 is different. In the illustrated example, the attribute 120 is a pattern of "X" symbols, spaced 0.25 inches apart but between the grid lines.

In one exemplary mode of operation, the hospital pharmacy dispenses the pain reliever Percocet in the pouch 66 shown in FIG. 3A. When the package 18 arrives in the patient's hospital room, the nurse can scan in the patient's bar coded information to positively identify the patient and access the patient's medical records, including prescribed medication. The GUI interface displays information regarding the patient, such as the medication schedule. At that point, the attribute 20 of the medication package 18 can be imaged and processed by the programmable control means 36, then correlated to the attribute library 64 for positive identification. If the attribute 20 of the medication package 18 intended for the patient correlates well with an attribute of a candidate medication in the attribute library 64, a positive identification is reported and a confirmation message can be sent to the output device 52, such as a description and/or image of the medication, or a confirmatory beep.

In another embodiment of the present invention, once the intended medication for the patient has been identified through the attribute library, the identified medication can be cross-checked against the patient's records in the database 62 to assure the proper medication is being administered. For example, turning to FIGS. 4A and 4B, the disclosed system can identify when a change in medication has occurred and alert the attending nurse. FIG. 4A illustrates a medication 216 in caplet form having a non-descript appearance, such as the reverse side of a Vicodin tablet. The hospital pharmacy may have deposited the Vicodin pill 216 in a pouch 266 consistent with normal protocol, but inadvertently placed the pill writing-side down. The attributes 220 of the packaging include: white, caplet, and solid circles printed on a grid 268, spaced at 0.5-inch intervals.

FIG. 4B illustrates a medication 316 that may easily be mistaken for medication 216. The pill 316 looks the same; namely, a white caplet, but may be a Tylenol caplet with the stamped name on the back side, out of view. In this example, the pharmacy may have placed the pill 316 in pouch 366 with the writing hidden from view. The attributes 320 include: white, caplet, and a pattern of "X" symbols printed on the pouch, spaced 0.25 inches apart but between the grid lines. In the event pouch 366 with medication 316 (e.g., the Tylenol caplet) was intentionally or unintentionally switched with pouch 266 and medication 216 (e.g., the Vicodin caplet), the optical imager 22 would correlate the attributes 320 with the attribute library 64 and report back that the intended medication was a Tylenol caplet. At this point, the identified medication 316 can be correlated to the patient's prescribed medication schedule in database 62, and the discrepancy can be reported back to the imager output device 52 in the form of a warning message or a beep, for example. In this manner, the intended medication for the patient can be correlated to the attribute library 64 to assure the proper medication is being dispensed at the proper interval.

Thus, the grid pattern and symbols on the pouch as well as the medication themselves offer useful variants for identifying medications. The attributes 20 on the pouch 66 may further identify classes of medication. For example, with reference to FIGS. 3B and 4B, the pattern of "X" symbols printed on the pouch, spaced 0.25 inches apart but between the grid lines, may indicate over-the-counter (e.g., uncontrolled) medication.

The package 18 containing the medication is not limited to a pouch. For example, current practice in many hospital pharmacies is to dispense medication in paper cups. Using the described embodiments disclosed herein, specialized paper cups can be utilized with attributes printed thereon. The paper cups (not shown) may include the grid pattern, the symbols, or both. In practice, the imager can image the pill within the cup and correlate the imaged attributes to the attribute library, as described above.

Another useful attribute 20 for the medication package 18 is pigment, or color. Pigmentation may be implemented either in external packaging, for example color-coded packages, or on the pill itself. In one embodiment, pigmentation can be mixed into the filler and/or binders of the medication 16 to give the pill a unique color. In another embodiment, pigmentation can be added to the coating on the medication 16. For example, pigment dyes may be utilized in the polymer- or polysaccharide-based coating of the pill. The optical imager 22 can be adapted to illuminate, image, and decode an attribute comprising colored inks, such as ultraviolet florescent inks.

In one embodiment of the present invention, the illumination assembly 24 of the optical imager 22 generates light, which as the term "light" is used herein means those electromagnetic wavelengths in the visible and non-visible spectrum. An example of these electromagnetic wavelengths can include ultraviolet ("UV") light, infra-red ("IR") light, other non-visible light, as well as other light selected based on the properties of the printing material used to create the attribute 20. These printing materials can comprise inks such as inks that, while not visible to the human eye, emit light when excited by the illuminating optics assembly 30. These inks are generally well-known and one skilled in the indicia reading arts will be readily able to understand the properties of the printing materials for use in printing the attribute 20 on the package 18. However, the disclosed embodiment may further include novel inks and the like integrated within the medication 16 itself. Thus, light from the illuminating optics assembly 30 that is compatible with the printing materials can emanate from light sources that comprise one or more light emitting diodes ("LEDs"). These LEDs can comprise LEDs of a single color (e.g., UV LEDs), or they can comprise differently colored LEDs, the light from which can be combined to so that the overall color emitted by the light source can be controlled and varied. In other embodiments, the illuminating optics assembly 30 can be operatively configured to generate laser light such as can be done with LEDs and/or laser diodes.

Although light from traditional techniques such as "blacklight" techniques (that utilize UV light) could be used to illuminate certain types of printing materials, this illumination may not permit the optical imager 22 to generate consistently good correlations between the attribute 20 and the corresponding attribute stored in the attribute library 64. Indeed, the use of UV light, IR light, and light of similar wavelength and/or frequency to illuminate the attribute can limit the operating characteristics of the imager because the imager oftentimes has to be placed in very near proximity to the attribute.

Referring back to FIG. 2, this deficiency may be overcome by incorporating an optical filter 70. The optical filter 70 can be provided in some embodiments with certain frequency pass-bands that match the emission wavelengths of the light emitted by the printing material. In other embodiments, the filter 70 can be provided with frequency pass-bands that match the emission wavelengths of the light emitting diodes (LEDs) in the illuminating optics assembly 30. While these pass-bands can be configured to pass light that has a wide range of wavelengths, it is contemplated that the optical filter 70 will comprise pass-bands that permit the light to pass to the image sensor 32, but effectively block all other wavelengths in the visible and invisible ranges. By way of non-limiting example, the optical filter 70 can be positioned between the medication package 18 and the image sensor 32 so that light emitted by (or reflected from) the package attribute 20 must pass through the optical filter before it reaches the image sensor. This position, when combined with construction of the optical filter that is based on the particular light source and/or the printing materials of the package attribute, can permit the optical imager to decode the attribute. This feature is beneficial because it permits the imager to be located in spaced relation, for example up to 20 cm away, to the attribute without degradation of its ability to achieve consistent good decodes of the encoded symbol character 12. An advantage of this arrangement is that the attributes may be invisible to the naked eye and only detectable by the imager, which discourages alteration. Another advantage is that patient medications can be color-coded to individual patients, which discourages mix-ups between patients in the same room.

The optical filter 70 can comprise a plurality of filter regions (not shown), each of which can be configured to permit a certain wavelength (or range of wavelengths) to pass onto the image sensor 32. Exemplary ranges can include, for example, wavelengths consistent with red, green, and orange visible light, or as defined by particular values of the passband wavelength such as 625 nm, 610 nm, and 510 nm, among others. The optical filter 70 can be constructed as a unitary structure made out of for example plastic (e.g., acrylic) that is treated and/or manufactured so as to include one or more of the filter regions. Other examples of the optical filter 70 can be constructed with a substrate which has deposited thereon certain types of optical materials (e.g., optical coatings, optical films, optical layers), which are particularly selected so as to form the filter regions. In other embodiments of the present invention, these optical materials can be disposed on, or constructed as part of, the image sensor 32 such as part of its lens assembly (not shown). This configuration can be implemented, in one example, by disposing optical materials on pixels (and regions of pixels) found in the pixel array.

Another useful attribute 20 for the medication package 18 is relative size. A feature on the medication pouch such as the grid pattern disclosed in FIGS. 3 and 4 can be useful in determining if the medication intended for the patient is the proper size. In one example, shown in FIG. 3A, the grid 68 printed on the upper portion of the package 18 can comprise squares spaced by a distance "d" of 0.25 inch, as described above. The symbols 20 printed on the pouch 66 can be recognized by the optical imager 22 and correlated to the attribute library 64, wherein the imager reports that the triangular symbols denote that grid spacing distance "d" is 0.25 inches. In this manner, when an image of the medication 16 is decoded, the width of the pill may be determined to be approximately two grid blocks, or 0.5 inches. In other examples, the symbols may denote that the grid distance "d" is smaller, or larger. Using the symbols to define the relative size of the grid allows the size of the medication pill to be used as an attribute.

In another example, the symbols themselves can be a measurement reference. For example, instead of a grid pattern, the attribute 20 can be a symbol of a certain dimensional size. In a pediatric application, the attribute 20 could be a symbol or icon familiar to a child, such as a puppy, kitten, pony, sailboat, race car, or the like. The icon could be printed a particular dimensional size, such a 0.5 inches, in order for the optical imager 22 to determine the relative size of the medication 16 about to be administered. The particular symbol or icon could further be used to associate a particular patient. In this manner, a child, upon admittance, could select a preferential symbol or icon, and that symbol or icon could be printed on all prescribed medications.

The attributes of the medication package described herein can be encoded in hierarchical order, printed on a sticker, and the sticker applied to the medication package. For example, an encoded attribute may comprise four individual attributes: type of package, shape of pill, size (or size range) of pill, and light wavelength (e.g., pigmentation). Each form of medication in the attribute library comprises a unique permutation of the individual attributes. Thus, if there existed eight types of packages, four shapes of pill, six ranges of pill size, and four different colors, the encoded attribute includes 8×4×6×4=768 permutations. Of course, more or less than four individual attributes can be utilized in the hierarchical sequence.

In another aspect, the pouches 66 stored in the pharmacy can have a plurality of attributes 20 printed on them in random order. With a large enough set of possible attributes, enough permutations may be generated to uniquely identify each pouch 66, similar to a fingerprint. For example, four attributes 20 may be chosen in hierarchical order such as symbol, color of symbol, size of symbol, and grid pattern size. In the example, there can be 20 possible types of symbol, 16 possible colors, 10 different symbol sizes, and 4 different grid pattern sizes resulting in 20×16×10×4=12,800 permutations. As medication 16 is dispensed into each pouch 66, the pharmacist can capture a digital image of the medication associated with the unique package, and enter the image into the attribute library 64, associating it with the particular patient to whom the medication is to be given. Then, upon dispensing to the patient, the intended medication can be cross-referenced to the image stored in the attribute library 64 for verification purposes. This particular example assures a high degree of reliability and minimizes the chain-of-custody risks.

One of the improvements of the present disclosure is that better chain of custody can be realized in the dispensing of medication from hospital pharmacies. The hospital pharmacy can place the medication in a package having distinct attributes that may be imaged and decoded by an optical scanner. Prior to administering the medication to a patient, the imaged attributes may be correlated with an attribute library stored in a database. The imager may report back the medication about to be administered as confirmation. Alternatively, the reported medication may be correlated with the patient's medication schedule to assure the proper medication is to be dispensed.

While the present invention has been described with reference to a number of specific embodiments, it will be understood that the true spirit and scope of the invention should be determined only with respect to claims that can be supported by the present specification. Further, while in numerous cases herein wherein systems and apparatuses and methods are described as having a certain number of elements it will be understood that such systems, apparatuses and methods can be practiced with fewer than the mentioned certain number of elements. Also, while a number of particular embodiments have been described, it will be understood that features and aspects that have been described with reference to each particular embodiment can be used with each remaining particularly described embodiment.

What is claimed is:

1. A system to correlate a medication package with a prescribed medication, the medication package accommodating medication for a patient, the system comprising:
   an optical imager that uses a two-dimensional image sensor array to read an encoded symbol comprising encoded patient information and further to image an attribute of the medication package, the optical imager comprising an imaging lens for focusing an image on the two-dimensional image sensor array, the two-dimensional image sensor array having a plurality of pixels formed in a plurality of rows and columns of pixels, the optical imager having a digital link to transmit a segment of data comprising the patient information encoded in the encoded symbol and the attribute of the medication package;
   a host computer connected to the digital link to receive the segment of data from the optical imager; and
   a database coupled to the host computer via a digital connection, the database to correlate the segment of data to (a) a patient record, and (b) a medication package attribute library;
   wherein the optical imager captures an image of a feature associated with the medication package, the feature selected from the group consisting of a pattern of symbols and a grid pattern, the feature having a predetermined size characteristic, and wherein the system processes the image using the predetermined size characteristic to determine a size of the medication.

2. The system of claim 1, wherein the patient record includes prescribed medication, and the attribute of the medication package correlates to the prescribed medication in the patient record.

3. The system of claim 1, wherein the medication package comprises the medication itself.

4. The system of claim 3, wherein the attribute of the medication package comprises the shape of the medication.

5. The system of claim 3, wherein the attribute of the medication package comprises the size of the medication.

6. The system of claim 1, wherein the attribute of the medication package is printed on the package.

7. The system of claim 6, wherein the printed attribute is a grid pattern.

8. The system of claim 7, wherein the attribute further comprises a symbol printed on the grid pattern.

9. The system of claim 1, wherein the attribute of the medication package comprises a pigmentation.

10. The system of claim 9, further comprising an optical filter positioned between the medication package and the two-dimensional image sensor array within the optical imager, the optical filter having a pass band for passing light of a wavelength emitted by an illumination source assembly in the optical imager.

11. The system of claim 9, wherein the pigmentation is ultraviolet.

12. The system of claim 1, wherein the attribute of the medication package comprises pigmentation mixed with the medication.

13. The system of claim 1, wherein the attribute of the medication package comprises pigmentation comprising a dye applied to a coating of the medication.

14. The system of claim 1, further comprising a plurality of attributes for the medication package, the plurality of attributes encoded in hierarchical order.

15. A method comprising the steps of:
   providing an optical imager comprising a two-dimensional image sensor array and an imaging lens for focusing an image on the two-dimensional image sensor array, the two-dimensional image sensor array having a plurality of pixels formed in a plurality of rows and columns of pixels;
   providing a medication, the medication being accommodated by a medication package, the package having an attribute;
   providing one or more database comprising patient identifiers associated to medications and an attribute library, the attribute library comprising a plurality of candidate medications that have been prescribed to a patient, each candidate medication having an associated package attribute;

reading with an optical reader an encoded symbol comprising encoded patient information for the patient;

capturing an image of the medication package with the optical imager wherein the optical imager captures an image of a feature associated with the medication package, the feature selected from the group consisting of a pattern of symbols and a grid pattern, the feature having a predetermined size characteristic;

processing the image to identify an attribute of the medication package, wherein the method processes the image using the predetermined size characteristic to determine a size of the medication;

accessing the attribute library and correlating the attribute of the medication package to the stored attributes of the candidate medications; and reporting, by the optical imager, information of medications of the patient and a match between the imaged attribute of the medication package and one of the candidate medications.

16. The method of claim 15, further comprising the steps of:

providing patient information in encoded symbol character format, the patient information correlating to a patient record in the database, the patient record comprising prescribed medication;

decoding and correlating the encoded symbol character to the patient record; and correlating, by the optical imager, the prescribed medication in the patient record with the medication for the patient.

17. The method of claim 16, further comprising the step of outputting user perceptible data via an output device on the optical imager.

18. The method of claim 15, wherein the step of capturing the image of the medication package comprises illuminating the package with a specific wavelength of light.

19. The method of claim 18, wherein the optical imager comprises an optical filter adapted to pass the specific wavelength of light and block all other wavelengths of light.

20. A system comprising:

a medical package having a pouch to hold a medication; and an optical imager comprising a two-dimensional image sensor array and an imaging lens for focusing an image on the two-dimensional image sensor array, the two-dimensional image sensor array having a plurality of pixels formed in a plurality of rows and columns of pixels, wherein the optical imager captures an image of a feature associated with the medication package, the feature selected from the group consisting of a pattern of symbols and a grid pattern, the feature having a predetermined size characteristic, and wherein the system processes the image using the predetermined size characteristic to determine a size of the medication.

* * * * *